(12) United States Patent
Shimono et al.

(10) Patent No.: US 10,081,589 B2
(45) Date of Patent: Sep. 25, 2018

(54) METHOD FOR MANUFACTURING α-BROMOACETOPHENONE COMPOUND

(71) Applicant: FUJIFILM Corporation, Tokyo (JP)

(72) Inventors: Katsuhiro Shimono, Kanagawa (JP); Katsuyuki Yofu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/292,151

(22) Filed: Oct. 13, 2016

(65) Prior Publication Data

US 2017/0029356 A1 Feb. 2, 2017

Related U.S. Application Data

(63) Continuation of application No. PCT/JP2015/061873, filed on Apr. 17, 2015.

(30) Foreign Application Priority Data

May 15, 2014 (JP) ................................ 2014-101626

(51) Int. Cl.
C07C 67/287 (2006.01)
C07C 45/63 (2006.01)

(52) U.S. Cl.
CPC ............ *C07C 67/287* (2013.01); *C07C 45/63* (2013.01); *C07C 2101/02* (2013.01); *C07C 2101/14* (2013.01)

(58) Field of Classification Search
None
See application file for complete search history.

(56) References Cited

U.S. PATENT DOCUMENTS

| 4,174,397 A * | 11/1979 | Knabe | C07C 45/63 514/366 |
|---|---|---|---|
| 4,559,371 A | 12/1985 | Husler et al. | |
| 4,739,052 A | 4/1988 | Husler et al. | |
| 4,861,916 A * | 8/1989 | Kohler | C07C 45/673 522/14 |
| 4,900,823 A | 2/1990 | Husler et al. | |
| 5,045,573 A | 9/1991 | Kohler et al. | |
| 7,683,096 B2 | 3/2010 | Nakamura et al. | |
| 8,093,241 B2 | 1/2012 | Nakamura et al. | |
| 2016/0200654 A1 | 7/2016 | Yofu et al. | |

FOREIGN PATENT DOCUMENTS

| JP | S59-167546 A | 9/1984 |
|---|---|---|
| JP | S62-502403 A | 9/1987 |
| JP | H06-228218 A | 8/1994 |
| JP | H06-322012 A | 11/1994 |
| JP | H11-511753 A | 10/1999 |
| JP | 2012-001451 A | 1/2012 |
| WO | 97/045420 A1 | 12/1997 |
| WO | 03/027059 A1 | 4/2003 |
| WO | 2015/045857 A1 | 4/2015 |

OTHER PUBLICATIONS

Cheung ("Acetic Acid" Ullmann's Encyclopedia of Industrial Chemistry, 2011, p. 209-237).*
International Search Report—PCT/JP2015/061873 dated Jul. 7, 2015.
International Preliminary Report on Patentability—PCT/JP2015/061873 completed Mar. 18, 2016.
An Office Action; "Notification of Reasons for Refusal," issued by the Japanese Patent Office dated May 23, 2017, which corresponds to Japanese Patent Application No. 2016-519179 and is related to U.S. Appl. No. 15/292,151; with English language translation.
An Office Action issued by Chinese Patent Office dated Mar. 30, 2018, which corresponds to Chinese Application No. 201580020362.X and is related to U.S. Appl. No. 15/292,151 with English language translation.

* cited by examiner

*Primary Examiner* — Jafar F Parsa
*Assistant Examiner* — Amy C Bonaparte
(74) *Attorney, Agent, or Firm* — Studebaker & Brackett PC

(57) ABSTRACT

A method for manufacturing an α-bromoacetophenone compound includes brominating a specific phenyl compound by reacting the specific phenyl compound with bromine in a solvent including at least one organic acid ester compound so as to obtain the α-bromoacetophenone compound that is a liquid at 5° C. to 30° C.

14 Claims, No Drawings

METHOD FOR MANUFACTURING α-BROMOACETOPHENONE COMPOUND

CROSS-REFERENCE TO RELATED APPLICATIONS

This application is a Continuation of PCT international Application No. PCT/JP2015/061873 filed on Apr. 17, 2015, which claims priority under 35 U.S.C § 119(a) to Japanese Patent Application No. 2014-101626 filed on May 15, 2014. Each of the above application(s) is hereby expressly incorporated by reference, in its entirety, into the present application.

BACKGROUND OF THE INVENTION

1. Field of the Invention

The present invention relates to a method for manufacturing an α-bromoacetophenone compound.

2. Description of the Related Art

An α-hydroxyacetophenone-based photopolymerization initiator is known as a polymerization initiator for a polymerizable compound having an ethylenically unsaturated bond. The α-hydroxyacetophenone-based photopolymerization initiator can be generally obtained by acylating a phenyl compound in the presence of Lewis acid by using carboxylic acid halide such as isobutyryl chloride, brominating an α carbon of this acyl group, and substituting this bromine atom with a hydroxyl group. With respect to the bromination reaction, JP1994-228218A (JP-H06-228218A) discloses brominating an α carbon of an isobutyryl group of 4-(2-acetoxyethoxy)-phenyl-2-propylketone or 4-hydroxyphenyl-2-propylketone. JP1994-322012A (JP-H06-322012A) discloses brominating an α carbon of an isobutyryl group of 4-methoxyisobutyrophenone.

SUMMARY OF THE INVENTION

However, in the bromination methods disclosed in JP1994-228218A (JP-H06-228218A) and JP1994-322012A (JP-H06-322012A), a certain amount of ring constituting carbon atoms of a benzene ring are brominated, in addition to the α carbon of an acyl group. Therefore, a purification step after reaction is required, but it is difficult to obtain a highly pure α-bromoacetophenone compound obtained by brominating only an α carbon of an acyl group without a purification process. In a case where a desired compound (that is, an α-bromoacetophenone compound, an α-hydroxyacetophenone compound derived from an α-bromoacetophenone compound, or the like) is a liquid compound having a low melting point, purification by recrystallization is difficult. In this manner, there are constraints in purification and high purity of the desired compound.

The photopolymerization initiator can be used in various ways. In addition to a use as a hardener component in paint, adhesives, an optical film, a solder resist material, and the like, uses requiring solubility in a solvent including water have widened. For example, in a case where a photopolymerization initiator is used as a curable ink component used in an ink jet printer, it is required to provide hydrophilicity by increasing polarity. In a case where an α-hydroxyacetophenone-based photopolymerization initiator is used as a photopolymerization initiator, it is possible to increase the hydrophilicity of the photopolymerization initiator by introducing a polar group such as an ethylene oxide chain in a specific chain length as a substituent on a benzene ring of a phenyl compound which is a synthesis raw material. However, if an ethylene oxide chain or the like is introduced, melting points of an α-halogenoacetophenone compound which is an obtained synthesis intermediate or an α-hydroxyacetophenone compound which is a desired photopolymerization initiator decrease and the α-halogenoacetophenone compound or the α-hydroxyacetophenone compound becomes liquid. In this case, purification by a recrystallization method cannot be performed.

An object of the invention is to provide a method for manufacturing a α-bromoacetophenone compound which is a liquid at 5° C. to 30° C. which is useful as a synthesis intermediate for a photopolymerization initiator having a specific polar group giving excellent reaction purity.

The object of the invention is solved by means as follows.

[1] A method for manufacturing an α-bromoacetophenone compound represented by Formula (2) below, comprising: brominating a phenyl compound represented by Formula (1) below by reacting the phenyl compound with bromine in a solvent including at least one organic acid ester compound, in which the α-bromoacetophenone compound is a liquid at 5° C. to 30° C.

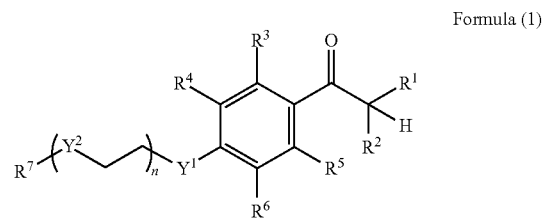

Formula (1)

In Formula (1), $R^1$ and $R^2$ each independently represent an alkyl group. $R^3$ to $R^6$ each independently represent a hydrogen atom or a substituent. However, at least one of $R^3$, $R^4$, $R^5$, or $R^6$ is a hydrogen atom. $Y^1$ and $Y^2$ each independently represent an oxygen atom or a sulfur atom, and n represents 2 to 3. $R^7$ represents a hydrogen atom, an alkyl group, an acyl group, or a trialkylsilyl group.

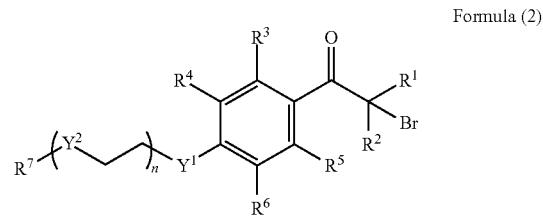

Formula (2)

In Formula (2), $R^1$ to $R^7$, $Y^1$, $Y^2$, and n each have the same meaning as $R^1$ to $R^7$, $Y^1$, $Y^2$, and n in Formula (1) above.

[2] The method for manufacturing an α-bromoacetophenone compound according to [1], in which a reaction temperature of the bromination is 20° C. or greater.

[3] The method for manufacturing an α-bromoacetophenone compound according to [1] or [2], in which the solvent including at least one organic acid ester compound is one or two or more selected from methyl acetate, ethyl acetate, butyl acetate, propyl acetate, and isopropyl acetate.

[4] The method for manufacturing an α-bromoacetophenone compound according to any one of [1] to [3], in which a reaction temperature of the bromination is 40° C. or greater.

[5] The method for manufacturing an α-bromoacetophenone compound according to any one of [1] to [4], in which a total content of the solvent including at least one organic acid ester compound is 50 to 100 mass % in a total amount of the solvent used in the bromination.

[6] The method for manufacturing an α-bromoacetophenone compound according to any one of [1] to [5], in which an amount of the solvent including at least one organic acid ester compound in a reaction liquid of the bromination is 0.5 to 60 mL per 1 g of the phenyl compound mixed into the reaction liquid.

[7] The method for manufacturing an α-bromoacetophenone compound according to any one of [1] to [6], in which the bromination is performed by adding bromine or a mixed liquid including bromine and the solvent including at least one organic acid ester compound dropwise into a mixed liquid including the phenyl compound and the solvent including at least one organic acid ester compound, or the bromination is performed by adding a mixed liquid including bromine and the solvent including at least one organic acid ester compound dropwise into the phenyl compound or the mixed liquid including the phenyl compound and the solvent including at least one organic acid ester compound.

[8] The method for manufacturing an α-bromoacetophenone compound according to [7], in which the bromination is performed by adding a mixed liquid including the bromine and the solvent including at least one organic acid ester compound dropwise into the mixed liquid including the phenyl compound and the solvent including at least one organic acid ester compound.

[9] The method for manufacturing an α-bromoacetophenone compound according to [8], in which a ratio of an amount A of the solvent including at least one organic acid ester compound in the mixed liquid including the bromine and the solvent including at least one organic acid ester compound and an amount B of the solvent including at least one organic acid ester compound in the mixed liquid including the phenyl compound and the solvent including at least one organic acid ester compound satisfies B:A=90:10 to 30:70 in a volume ratio.

According to the manufacturing method according to the invention, a α-bromoacetophenone compound which is a liquid at 5° C. to 30° C. and which generally does not require a purification process such as recrystallization can be obtained with high reaction purity.

DESCRIPTION OF THE PREFERRED EMBODIMENTS

The method for manufacturing an α-bromoacetophenone compound according to the invention (hereinafter, simply referred to as a "manufacturing method according to the invention") is described in detail.

The manufacturing method according to the invention uses a phenyl compound represented by Formula (1) below, as a starting material.

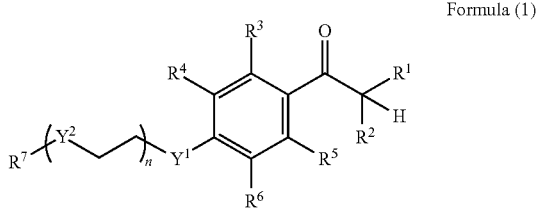

Formula (1)

In Formula (1), $R^1$ and $R^2$ each independently represent an alkyl group. This alkyl group may be linear or branched. $R^1$ and $R^2$ are alkyl groups preferably having 1 to 10 carbon atoms, more preferably having 1 to 5 carbon atoms, even more preferably having 1 to 3 carbon atoms, are even more preferably methyl or ethyl, and most preferably methyl.

$R^1$ and $R^2$ may be linked to each other to form a ring. A group in a ring structure formed by linking $R^1$ and $R^2$ is preferably a cycloalkyl group. This cycloalkyl group is a cycloalkyl group more preferably having 3 to 10 carbon atoms, and even more preferably having 4 to 8 carbon atoms, and specifically, $R^1$ and $R^2$ are preferably cyclopropyl, cyclobutyl, cycloheptyl, or cyclohexyl.

In Formula (1), $R^3$ to $R^6$ each independently represent a hydrogen atom or a substituent. However, at least one of $R^3$, $R^4$, $R^5$, or $R^6$ is a hydrogen atom. It is preferable that two or more of $R^3$ to $R^6$ (preferably, two or more including $R^4$ and $R^6$) are hydrogen atoms, it is more preferable that three or more thereof (preferably, three or more including $R^4$ and $R^6$) are hydrogen atoms, and it is even more preferable that all of $R^3$ to $R^6$ are hydrogen atoms.

In a case where $R^3$ to $R^6$ are substituents, examples of these substituent include an alkyl group (an alkyl group preferably having 1 to 5 carbon atoms, more preferably having 1 to 3 carbon atoms, and even more preferably having 1 or 2 carbon atoms), a halogen atom (specifically, a fluorine atom, a chlorine atom, a bromine atom, or an iodine atom), an amino group, a hydroxyl group, a cyano group, a nitro group, a carboxyl group, a sulfo group, a sulfonyl group, a phosphonyl group, a boric acid group, an alkoxy group, and an amido group. Among these, methyl, ethyl, or a halogen atom is preferable.

In Formula (1), $R^7$ represents a hydrogen atom, an alkyl group, an acyl group, or a trialkylsilyl group. $R^7$ is more preferably an acyl group.

In a case where $R^7$ is an alkyl group, the alkyl group may be linear or branched and may have a substituent. This alkyl group preferably has 1 to 10 carbon atoms, more preferably has 1 to 6 carbon atoms, and even more preferably has 1 to 5 carbon atoms. In a case where $R^7$ is an alkyl group, the substituent that this alkyl group has may be linked to form a ring structure. Examples of the alkyl group that forms a ring structure in this manner include 2-tetrahydropyranyl. In a case where $R^7$ is an alkyl group, the alkyl group is preferably an alkoxymethyl group (an alkoxymethyl group preferably having 1 to 10 carbon atoms and more preferably having 1 to 5 carbon atoms). Preferable examples in a case where $R^7$ is an alkyl group include methyl, ethyl, propyl, isopropyl, t-butyl, methoxymethyl, ethoxymethyl, benzyl, p-methoxybenzyl, phenethyl, and 2-tetrahydropyranyl, and more preferable examples include methyl, methoxymethyl, benzyl, or 2-tetrahydropyranyl.

In a case where $R^7$ is an acyl group, the number of carbon atoms thereof is preferably 2 to 12, more preferably 2 to 10, and even more preferably 2 to 6. $R^7$ is more preferably acetyl, pivaloyl, acryloyl, or benzoyl and even more preferably acetyl.

In a case where $R^7$ is a trialkylsilyl group, an alkyl group of a trialkylsilyl group may be linear or branched. This alkyl group preferably has 1 to 10 carbon atoms, more preferably has 1 to 6 carbon atoms, and even more preferably has 1 to 4 carbon atoms. Specifically, examples thereof include trimethylsilyl, triethylsilyl, t-butyldimethylsilyl, and triisopropylsilyl. $R^7$ is preferably trimethylsilyl.

In Formula (1), $Y^1$ and $Y^2$ each independently represent an oxygen atom or a sulfur atom, and it is more preferable that $Y^1$ and $Y^2$ are oxygen atoms.

In Formula (1), n represents 2 to 3 and preferably represents 2. If n represents 2 or 3, the compound of Formula (2) which is a reaction product of the bromination (bromination reaction) is generally a liquid at 5° C. to 30° C. If n represents 0 to 1, regioselectivity of a bromination in the bromination reaction decreases. It is difficult to cause physical properties of the compound of Formula (2) which is a reaction product to be in the range determined in the invention.

A method for synthesizing the phenyl compound represented by Formula (1) is not particularly limited and can be obtained in a common method. For example, the phenyl compound can be obtained by causing an acylating agent represented by Formula (1-b) below to react with a compound represented by Formula (1-a) below in the presence of Lewis acid of aluminium (III) chloride or the like.

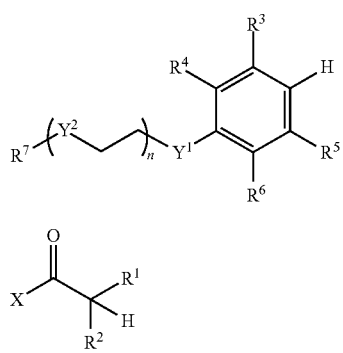

Formula (1-a)

Formula (1-b)

In Formulae (1-a) and (1-b), $R^1$ to $R^7$, $Y^1$, $Y^2$, and n each have the same meaning as $R^1$ to $R^7$, $Y^1$, $Y^2$, and n in Formula (1), and preferable embodiments are also the same. X represents a halogen atom, and preferably a chlorine atom or a bromine atom.

The phenyl compound represented by Formula (1) above is as described above and is generally a liquid at 5° C. to 30° C. If the compound of Formula (1) above is a liquid at 5° C. to 30° C., it is possible to cause the compound of Formula (2) below obtained by acylating the phenyl compound of Formula (1) above to be a liquid at 5° C. to 30° C. The expression "a compound is a liquid at 5° C. to 30° C." according to the invention means that a crystal is not precipitated even if the compound is left for one week in an atmosphere of 5° C. to 30° C. under normal pressure.

Specific examples of the phenyl compound represented by Formula (1) above are provided below, but the invention is not limited thereto.

1a

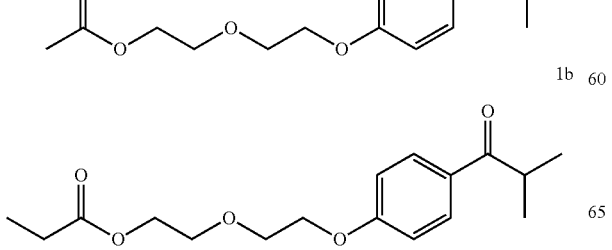

1b

1c
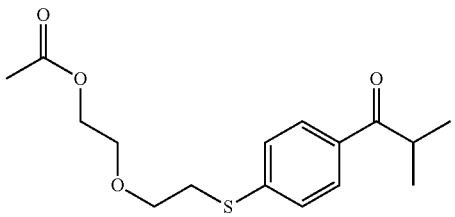

1d

1e
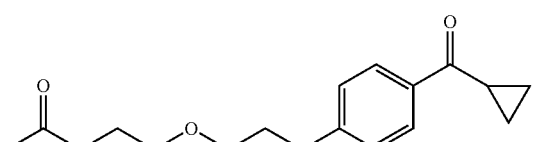

1f
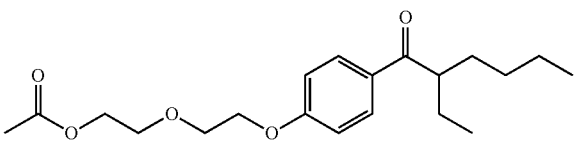

1g
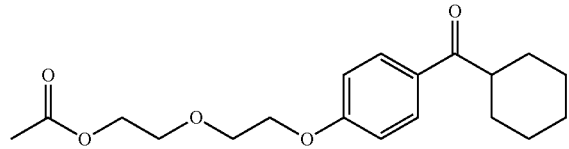

1i
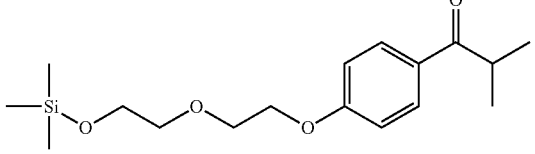

1j

1k
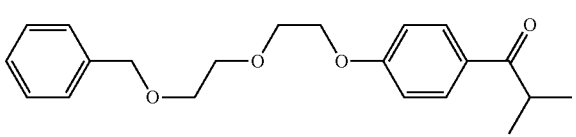

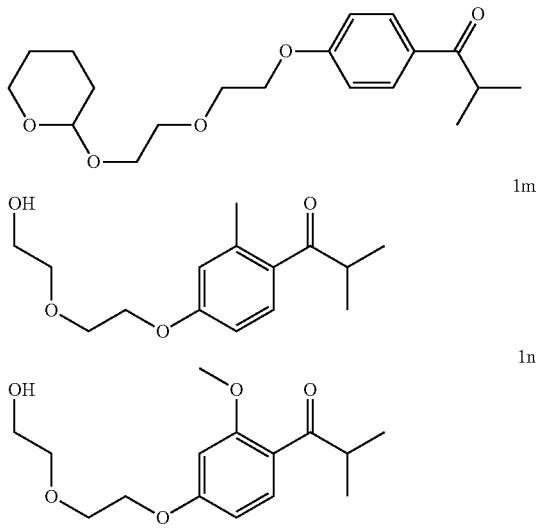

In the manufacturing method according to the invention, the phenyl compound represented by Formula (1) above and bromine are caused to react with each other in a specific reaction temperature by using a specific solvent. Accordingly, the α-bromoacetophenone compound that is represented by Formula (2) below and is a liquid at 5° C. to 30° C. can be generally obtained with high purity in about 95% to 100% without a specific purification process.

Since the α-bromoacetophenone compound represented by Formula (2) below that can be obtained by the manufacturing method according to the invention is a liquid at a low temperature of 30° C. or lower, the α-bromoacetophenone compound is a compound that is difficult for purification by a general recrystallization method. However, by the manufacturing method according to the invention, in the bromination reaction of the phenyl compound of Formula (1), bromination reaction of a ring constituting carbon atom of a benzene ring can be greatly suppressed. Accordingly, it is possible to obtain the α-bromoacetophenone compound of Formula (2) below with high purity without providing a reaction product obtainable by the bromination reaction above to the purification process such as recrystallization.

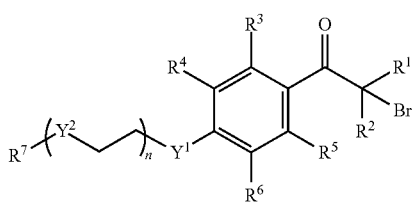

Formula (2)

In Formula (2) above, $R^1$ to $R^7$, $Y^1$, $Y^2$, and n each have the same meaning as $R^1$ to $R^7$, $Y^1$, $Y^2$, and n in Formula (1), and preferable embodiments are also the same.

Solvent

In the manufacturing method according to the invention, the phenyl compound represented by Formula (1) above and bromine are reacted in the solvent including at least one organic acid ester compound. If at least one organic acid ester compound is used as a solvent, the solvent used in this bromination reaction may include a compound other than the organic acid ester compound in the solvent. The solvent may include an ether compound without a hydroxyl group.

If a solvent including at least one organic acid ester compound is used, bromination reaction (side reaction) of a benzene ring that the phenyl compound of Formula (1) has is greatly suppressed, and thus a desired compound can be obtained with excellent purity. The reason thereof is not clear, but is assumed as follows.

In the bromination reaction of the phenyl compound of Formula (1), it is assumed that bromination of the benzene ring which is side reaction occurs due to reaction between $\delta^+$ of bromine (corresponding to bromocation) and a benzene ring. However, according to the invention, in a case where an organic acid ester compound or an ether compound without a hydroxyl group is used as the solvent in the bromination reaction, it is assumed that $\delta^+$ is trapped in a solvent, the solvent coordinates with $\delta^+$ of bromine via an oxygen atom constituting an ester bond or an ether bond, such that bromination reaction of the benzene ring hardly occurs. Even if a solvent has an oxygen atom in a molecule structure, in a case where the solvent is a protonic solvent such as alcohol or acetic acid, the side reaction above cannot be effectively suppressed. It is assumed that this is because, if the solvent coordinates with a proton generated from the solvent via an oxygen atom itself, it becomes difficult for the solvent to coordinate with $\delta^+$ of bromine.

The organic acid ester compound that is used as a solvent in the manufacturing method according to the invention is not particularly limited, and examples thereof include methyl acetate, ethyl acetate, propyl acetate, isopropyl acetate, butyl acetate, hexyl acetate, methyl propionate, ethyl propionate, propyl propionate, isopropyl propionate, butyl propionate, hexyl propionate, methyl butyrate, ethyl butyrate, propyl butyrate, methyl isobutyrate, ethyl isobutyrate, propyl isobutyrate, γ-butyrolactone, ε-caprolactone, ethylene carbonate, propylene carbonate, 2-acetoxy-1-methoxypropane, methyl-3-methoxypropionate, cellosolve acetate, carbitol acetate, triethylene glycol diacetate, and dimethyl adipate, and one or two or more of these can be used. Among these, it is preferable to use one or two or more selected from methyl acetate, ethyl acetate, butyl acetate, propyl acetate, and isopropyl acetate.

The "organic acid ester compound" used as a solvent according to the invention includes an ether bond in this molecule structure in some cases. That is, a solvent having both of the ester bond of the organic acid and the ether bond in the molecule structure is included in an "organic acid ester compound". That is, the ether compound according to the invention is a solvent including an ether bond and not including an ester bond of an organic acid.

In the manufacturing method according to the invention, the ether compound without a hydroxyl group that can be used as a solvent is not particularly limited, and examples thereof include diethyl ether, diethylene glycol dimethyl ether, dipropyl ether, dibutyl ether, dihexyl ether, ethylene glycol diethyl ether, diethylene glycol dimethyl ether, isoamyl ether, diethylene glycol diethyl ether, triethylene glycol dimethyl ether, tetraethylene glycol dimethyl ether, diethylene glycol methylethyl ether, methyl tertiary butyl ether, diethylene glycol dibutyl ether, 1,4-dioxane, and tetrahydrofuran, and one or two or more of these can be used. Among these, one or two or more selected from diethylene glycol methyl ether, dipropyl ether, dibutyl ether, dihexyl ether, ethylene glycol diethyl ether, diethylene glycol dimethyl ether, isoamyl ether, diethylene glycol diethyl ether, triethylene glycol dimethyl ether, tetraethylene glycol dimethyl ether, diethylene glycol methylethyl ether, diethylene glycol dibutyl ether, and 1,4-dioxane are preferably used, and 1,4-dioxane is more preferably used.

In view of workability such as volatility and liquid separability, the solvent used in the bromination reaction according to the invention is preferably one or two or more selected from methyl acetate, ethyl acetate, butyl acetate, propyl acetate, isopropyl acetate, methyl propionate, and ethyl propionate, and more preferably one or two or more selected from methyl acetate, ethyl acetate, butyl acetate, propyl acetate, and isopropyl acetate.

As described above, as long as the solvent used at the time of bromination reaction according to the invention includes a solvent selected from an organic acid ester compound and an ether compound without a hydroxyl group, the solvent may include a solvent other than an organic acid ester compound and an ether compound without a hydroxyl group. The solvent other than the organic acid ester compound and the ether compound without a hydroxyl group is not particularly limited. For example, a solvent selected from ketone, alcohol, dialkylformamide, N-alkylpyrrolidone, and toluene can be used, but the invention is not limited to these aspects, and a solvent that is generally used in the bromination reaction can be widely used. According to the invention, in the total amount of the solvent used at the time of the bromination reaction, a total content of the solvent including at least one organic acid ester compound is preferably 50 to 100 mass %, more preferably 70 to 100 mass %, and even more preferably 80 to 100 mass %.

In the manufacturing method according to the invention, the phenyl compound represented by Formula (1) above is provided in the bromination reaction in a coexistence state with the specific solvent above. In the reaction liquid of the bromination reaction (that is, in the reaction liquid in which all of the solvent, bromine, and the phenyl compound which is a reactant are mixed), an amount of the solvent including at least one organic acid ester compound is preferably 0.1 mL or greater, more preferably 0.3 to 120 mL, also preferably 0.5 to 60 mL, also preferably 0.5 to 10 mL, and also preferably 0.5 to 5 mL per 1 g of the phenyl compound mixed into the reaction liquid of the bromination reaction. If a ratio of the solvent above and the phenyl compound above is caused to be in the preferable ratio above, the bromination reaction (side reaction) of the phenyl compound represented by Formula (1) above to the benzene ring can be more effectively suppressed, and bromination reaction to a desired site (an α carbon of acyl group) more effectively proceeds.

In the manufacturing method according to the invention, a ratio of the phenyl compound represented by Formula (1) above used in the bromination reaction and bromine is determined by a stoichiometric ratio. However, [bromine]/[phenyl compound of Formula (1)] is preferably 0.95 to 1.3, more preferably 1.0 to 1.2, and even more preferably 1.0 to 1.1 in a molar ratio.

In the manufacturing method according to the invention, the reaction temperature of the bromination reaction is not limited. However, the reaction temperature is preferably 10° C. or higher, more preferably 20° C. or higher, even more preferably 30° C. or higher, even more preferably 35° C. or higher, and most preferably 40° C. or higher. The reaction temperature of the bromination reaction is preferably a temperature close to a boiling point of bromine and a temperature of the boiling point or lower. Specifically, the reaction temperature is preferably 60° C. or lower and more preferably 55° C. or lower. Accordingly, selectivity of a bromination increases, and thus purity of the obtained compound of Formula (2) greatly increases.

Desired reaction of an acyl group at an α position is promoted by increasing the reaction temperature, and thus excess bromine in a reaction system is small. Therefore, it is assumed that side reaction with a benzene ring becomes difficult to proceed, and selectivity of the desired reaction of the acyl group at an α position is improved.

In the manufacturing method according to the invention, a reaction time of the bromination reaction is not particularly limited. However, the reaction time is preferably 15 minutes or longer from the start of the reaction (that is, from the start of the mixing of bromine and the phenyl compound of Formula (1)) and more preferably 30 minutes or longer. The reaction time of the bromination reaction is generally within five hours and preferably within three hours.

The bromination is preferably performed in the dropwise addition reaction. This dropwise addition reaction is described below.

In a case where the bromination reaction in the manufacturing method according to the invention is performed by dropwise addition reaction, the preferable aspects include aspects as follows.

(I) An aspect of performing bromination reaction by feeding bromine into a dropwise addition funnel and adding this bromine dropwise to a mixed liquid (preferably a liquid obtained by dissolving the phenyl compound represented by Formula (1) above in a solvent including an organic acid ester compound, the same applies hereinafter) including the phenyl compound represented by Formula (1) above and a solvent selected from an organic acid ester compound and an ether compound without a hydroxyl group (II) An aspect of performing bromination reaction by feeding a mixed liquid including bromine and a solvent selected from an organic acid ester compound and an ether compound without a hydroxyl group (preferably a liquid obtained by dissolving bromine in a solvent including a solvent selected from an organic acid ester compound and an ether compound without a hydroxyl group, the same applies hereinafter) to a dropwise addition funnel and adding this mixed liquid dropwise into a phenyl compound (liquid) represented by Formula (1) above (III) An aspect of performing bromination reaction by feeding a mixed liquid including bromine and a solvent selected from an organic acid ester compound and an ether compound without a hydroxyl group into a dropwise addition funnel and adding this mixed liquid dropwise into a mixed liquid including the phenyl compound represented by Formula (1) above and a solvent selected from an organic acid ester compound and an ether compound without a hydroxyl group Among these, Aspect (I) or (III) above is preferable, and Aspect (III) is more preferable. In Aspect (III) above, a solvent mixed with bromine and a solvent mixed with the compound represented by Formula (1) above may be identical to or different from each other.

In the dropwise addition reaction above, the aforementioned reaction temperature of the bromination reaction according to the invention is set to be a temperature of a liquid (liquid including the compound represented by Formula (1)) on a dropwise added side. For example, in a reaction system in which the compound represented by Formula (1) or a mixed liquid of this compound and a solvent are fed into a reaction container such as a flask or a reaction tank, a dropwise addition funnel is provided, and bromine or a mixed liquid of bromine and a solvent is added dropwise, a temperature of the liquid in the reaction container is the reaction temperature of the bromination reaction according to the invention.

In the dropwise addition reaction above, dropwise addition time is not particularly limited and is appropriately adjusted according to consumption of dropwise added bromine. In view of further increasing selectivity of a bromination, the dropwise addition time is preferably one minute or longer, more preferably 15 minutes or longer, and even more preferably 30 minutes or longer. In the same point of view, the dropwise addition time is preferably within 180 minutes, more preferably within 120 minutes, even more preferably within 90 minutes, and even more preferably within 60 minutes. The dropwise addition is preferably performed during stirring the reaction liquid.

Even after the dropwise addition is completed, stirring is generally continued for about 30 minutes to 5 hours, so as to age the reaction. The stirring time after dropwise addition is completed is more preferably caused to be 1 hour to 3 hours.

With respect to starting time of dropwise addition of the dropwise addition reaction above, a ratio between the amount A of the solvent including at least one organic acid ester compound in the dropwise addition liquid including bromine and the amount B of the solvent including at least one organic acid ester compound in the liquid including the phenyl compound of Formula (1) is not particularly limited, but B:A (volume ratio) is preferably 100:0 to 10:90, more preferably 100:0 to 20:80, even more preferably 90:10 to 30:70, even more preferably 80:20 to 40:60, and even more preferably 70:30 to 50:50.

A total solvent amount with respect to 1 g of the reactant (phenyl compound) of Formula (1) used in the dropwise addition reaction above is not particularly limited, but if the total solvent amount with respect to the reactant is small, the side reaction easily occurs. There is no problem in the reaction regarding to the fact that the total solvent amount becomes great. However, in view of manufacturing cost, a total solvent amount that is too great is not preferable. The total solvent amount with respect to 1 g of the reactant of Formula (1) is preferably 0.7 ml, to 120 mL, more preferably 1.0 mL to 120 mL, even more preferably 1.5 mL to 120 mL, and most preferably 2 mL to 120 mL.

Specific examples of the compound represented by Formula (2) above which is a liquid at 5° C. to 30° C. are provided below, but the invention is not limited thereto.

2a

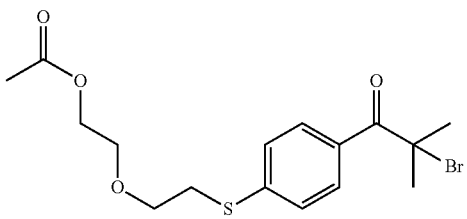

2b

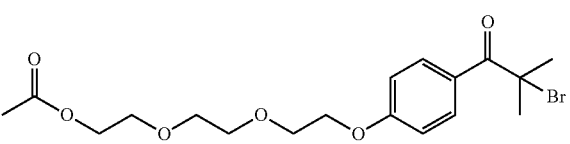

2c

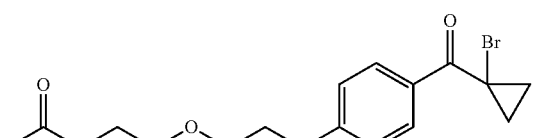

2d

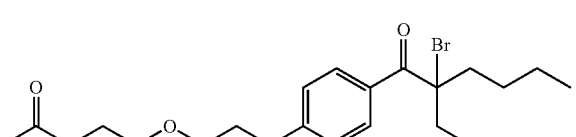

2e

2f

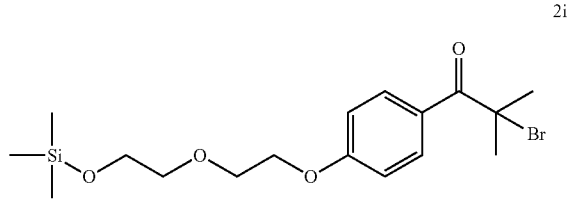

2g

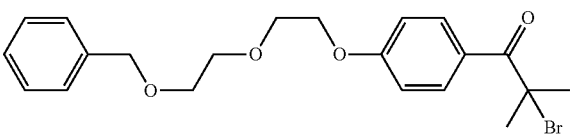

2i

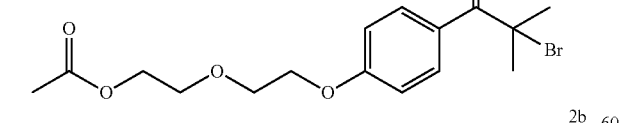

2j

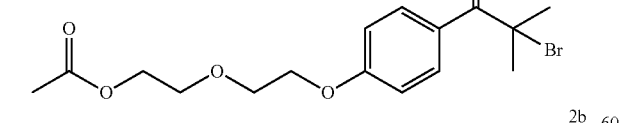

2k

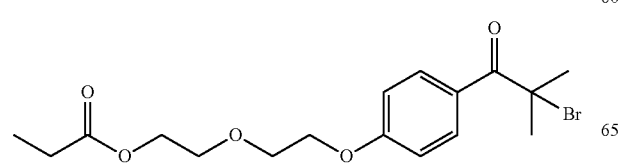

-continued

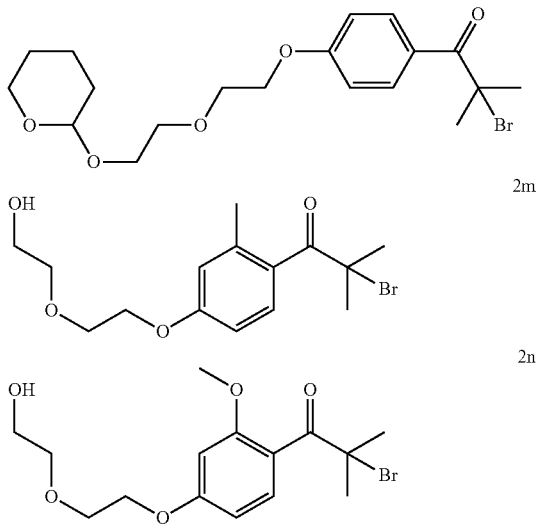

The α-bromoacetophenone compound represented by Formula (2) is particularly suitable as a synthesis intermediate of a photopolymerization initiator.

That is, if the α-bromoacetophenone compound represented by Formula (2) and a base are reacted to each other, it is possible to obtain a compound represented by Formula (3) below. It is preferable that this reaction is performed by adding water. This compound represented by Formula (3) can be suitably used as a photopolymerization initiator, particularly, a radical polymerization initiator, or a precursor thereof.

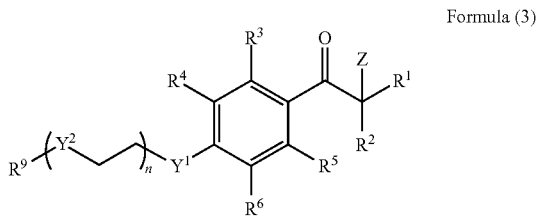

Formula (3)

In Formula (3), $R^1$ to $R^6$, $Y^1$, $Y^2$, and n each have the same meaning as $R^1$ to $R^6$, $Y^1$, $Y^2$, and in Formula (1) above, and preferable embodiments are also the same. $R^9$ represents a hydrogen atom, an alkyl group (an alkyl group preferably having 1 to 10 carbon atoms, more preferably having 1 to 5 carbon atoms, and even more preferably having 1 to 3 carbon atoms), an acyl group (an acyl group preferably having 2 to 10 carbon atoms, more preferably having 2 to 6 carbon atoms, and even more preferably having 2 to 4 carbon atoms), or a trialkylsilyl group (a trialkylsilyl group preferably having 1 to 10 carbon atoms, more preferably 1 to 5 carbon atoms, and even more preferably 1 or 2 carbon atoms, with respect to one alkyl group of the trialkylsilyl group). Z represents a hydroxyl group, an alkoxy group (an alkoxy group preferably having 1 to 10 carbon atoms, more preferably having 1 to 5 carbon atoms, and even more preferably having 1 to 3 carbon atoms), or an alkylamino group (including a dialkylamino group. An alkylamino group preferably has 1 to 10 carbon atoms, more preferably has 1 to 5 carbon atoms, and even more preferably has 1 to 3 carbon atoms, with respect to one alkyl group of an alkylamino group).

Examples of the base above include sodium hydroxide, potassium hydroxide, calcium hydroxide, lithium hydroxide, cesium hydroxide, rubidium hydroxide, sodium alkoxide (for example, sodium methoxide and sodium ethoxide), and alkyl amine.

If reaction with the α-bromoacetophenone compound is performed, for example, by using sodium hydroxide as a base and adding a sodium hydroxide aqueous solution, Z in Formula (3) can be caused to be a hydroxyl group. In this case, if $R^7$ of Formula (2) is an acyl group, the acyl group is hydrolyzed, and thus $R^9$ of Formula (3) becomes a hydrogen atom.

If sodium oxide is used as a base, Z in Formula (3) can be caused to be an alkoxy group.

If alkylamine is used as a base, Z in Formula (3) can be caused to be an alkylamino group.

The use amount of the base is preferably 1 to 50 and more preferably 5 to 20 by a molar ratio, with respect to one α-bromoacetophenone compound.

In the reaction between the α-bromoacetophenone compound represented by Formula (2) and the base, it is preferable to use a mixed solvent of water and a water soluble organic solvent. Examples of this water soluble organic solvent include glycerin, alkane diol (polyhydric alcohols) such as 1,2,6-hexanetriol, trimethylolpropane, ethylene glycol, and propylene glycol; sugar alcohols; alkylalcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-isopropyl ether, diethylene glycol mono-isopropyl ether, ethylene glycol mono-n-butyl ether, ethylene glycol mono-t-butyl ether, diethylene glycol mono-t-butyl ether, triethylene glycol monoethyl ether, 1-methyl-1-methoxybutanol, propylene glycol mono methyl ether, propylene glycol monoethyl ether, propylene glycol mono-t-butyl ether, propylene glycol mono-n-propyl ether, propylene glycol mono-isopropyl ether, dipropylene glycol, dipropylene glycol monomethyl ether, dipropylene glycol monoethyl ether, dipropylene glycol mono-n-propyl ether, dipropylene glycol mono-isopropyl ether, and tripropylene glycol monomethyl ether. Among these, in view of volatilization removability, it is preferable to use alcohol having 1 to 4 carbon atoms (for example, one or two or more selected from ethanol, methanol, butanol, propanol, and isopropanol).

The reaction between the α-bromoacetophenone compound represented by Formula (2) and the base is preferably performed at 10° C. to 40° C. The reaction time of this reaction is preferably 0.5 to 5 hours.

Hereinafter, the invention is described in detail with reference to examples, but the invention is not limited to the examples.

EXAMPLES

Reference Example 1

As the compound represented by Formula (1), a compound 1a below was synthesized by a scheme 1 below.

15

Scheme 1

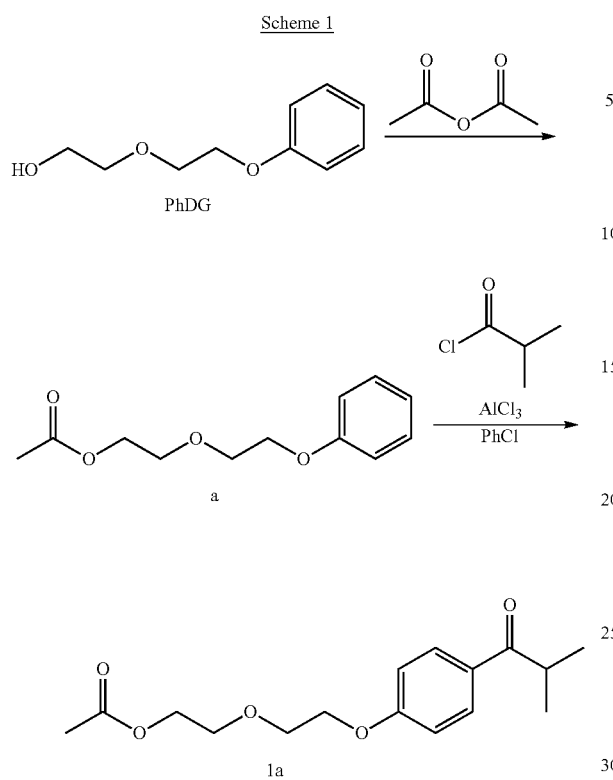

16

Example 1

Synthesis of Compound 2a

Scheme 2

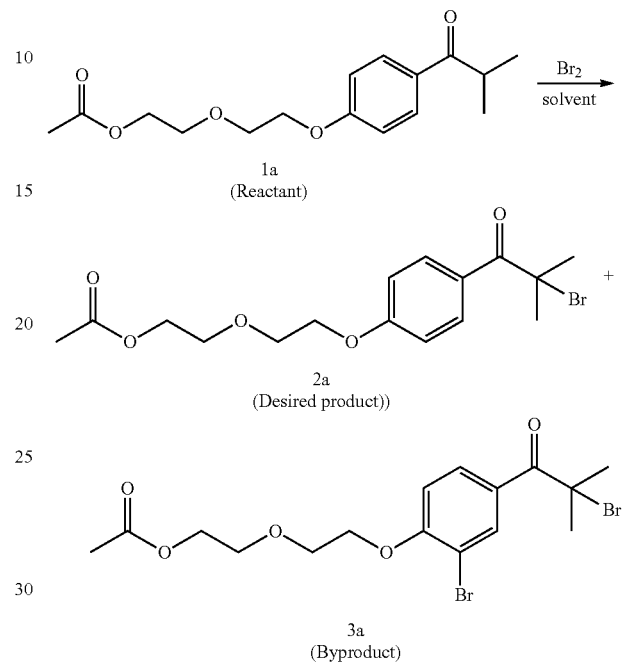

Synthesis of Compound a 97.2 g of acetic anhydride (0.95 mol) was added dropwise to 170.0 g of phenyl diglycol (PhDG, manufactured by Nippon Nyukazai Co, Ltd.) (0.93 mol) heated to 90° C. and was heated and stirred for six hours at 120° C. Thereafter, concentration was performed under reduced pressure, so as to obtain 204.4 g of a compound a (yield: 98%).

$^1$H-NMR (CDCl$_3$)

δ: 2.10 (3H, s), 3.78 (2H, m), 3.87 (2H, m), 4.15 (2H, m), 4.26 (2H, m), 6.90-6.98 (3H, m), 7.25-7.32 (2H, m)

Synthesis of Compound 1a 10.0 g of the compound a (44.59 mmol) was dissolved in 40 mL of chlorobenzene, was cooled to 5° C. in an ice bath, and 17.84 g of aluminum (III) chloride (133.78 mmol) was added. Thereafter, 5.59 mL of isobutyryl chloride (53.51 mmol) was added dropwise and was stirred for one hour. Subsequently, a reaction liquid was poured to 80 g of ice, a product was extracted with 40 mL of ethyl acetate, and an organic layer was sequentially washed with 80 mL of sodium bicarbonate water and 40 mL of salt water and was dried by using 10 g of magnesium sulfate. After this was filtrated, the filtrate was concentrated under reduced pressure, so as to obtain 11.87 g of the compound 1a (yield: 90%). The compound 1a was a liquid at 30° C.

$^1$H-NMR (CDCl$_3$)

δ: 1.20 (3H, s), 1.21 (3H, s), 2.10 (3H, s), 3.52 (1H, m), 3.78 (2H, m), 3.89 (2H, m), 4.20 (2H, m), 4.27 (2H, m), 6.97 (2H, d), 7.95 (2H, d)

10.0 g of the compound 1a (0.034 mol) and 12.5 mL of ethyl acetate were added to a three-neck flask having capacity of 100 mL provided with a dropwise addition funnel and a thermometer, a liquid temperature in a three-neck flask was adjusted to 45° C., and stirring was performed. 12.5 mL of ethyl acetate and 5.7 g of bromine (0.036 mol) were mixed, and the mixed liquid was added to the dropwise addition funnel, was added dropwise for 30 minutes, and was stirred for two hours. Meanwhile, temperature of the reaction liquid in the three-neck flask was continuously maintained at 45° C. Subsequently, 7 mL of a 3 wt % aqueous solution of sodium hydrogen sulfite was added dropwise into the solution after stirring, and the organic layer was sequentially washed with an aqueous solution of sodium hydrogen carbonate and saturated saline solution and was dried by using magnesium sulfate. After this was filtrated, the filtrate was concentrated under reduced pressure, so as to obtain 11.6 g of a compound 2a (reaction product) (yield: 91%). Both of the compounds 1a and 2a were liquids at 5° C. to 30° C.

$^1$H-NMR (CDCl$_3$)

δ: 2.04 (6H, s), 2.08 (3H, s), 3.79 (2H, m), 3.85 (2H, m), 4.21 (2H, m), 4.26 (2H, m), 6.94 (2H, d), 8.21 (2H, d)

In order to examine purity of the compound 2a obtained above, mol % of the compound 1a (reactant), the compound 2a (desired product), and a compound 3a (byproduct) that exist in the reaction product were calculated by expressions below, respectively based on peak areas at 7.95 ppm, 8.21 ppm, and 8.41 ppm of $^1$H-NMR (CDCl$_3$).

[mol % of reactant]=100×[peak area at 7.95 ppm]/{[peak area at 7.95 ppm]+[peak area at 8.21 ppm]+[peak area at 8.41 ppm]}

[mol % of desired product]=1.00×[peak area at 8.21 ppm]/{[peak area at 7.95 ppm]+[peak area at 8.21 ppm]+[peak area at 8.41 ppm]}

[mol % of byproduct]=100×[peak area at 8.41 ppm]/{[peak area at 7.95 ppm]+[peak area at 8.21 ppm]+[peak area at 8.41 ppm]}

Results are provided in a table below.

Examples 2 to 38, and 43 to 45

In the synthesis of the compound 2a in Example 1, the compounds 2a in Examples 2 to 38 and 43 to 45 were obtained in the same manner as in the synthesis of the compound 2a of Example 1, except for changing the reaction condition to reaction conditions provided in the table below. The purity of the obtained compounds 2a was measured in the same manner as in Example 1. Results thereof are provided in the table below.

Example 39

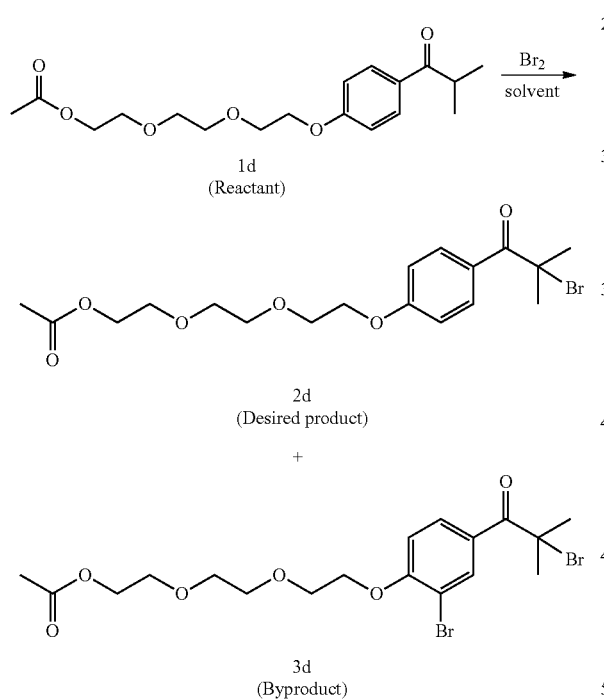

In the synthesis of the compound 2a in Example 1, a compound 2d was obtained in the same manner as in the synthesis of the compound 2a in Example 1 except for using a compound 1d instead of the compound 1a and changing the reaction condition to a reaction condition provided in the table below. In Reference Example 1 above, the compound 1d was synthesized in the same manner as in Reference Example 1 except for using phenyl triglycol (synthesized in a method disclosed in Tetrahedron 1988, 44, 5, pages 1553 to 1558) instead of PhDG. Both of the compounds 1d and 2d were liquids at 5° C. to 30° C.

Purity of the obtained compound 2d was calculated based on a peak ratio of $^1$H-NMR (CDCl$_3$) in the same manner as in Example 1. Results thereof are provided in the table below.

Example 40

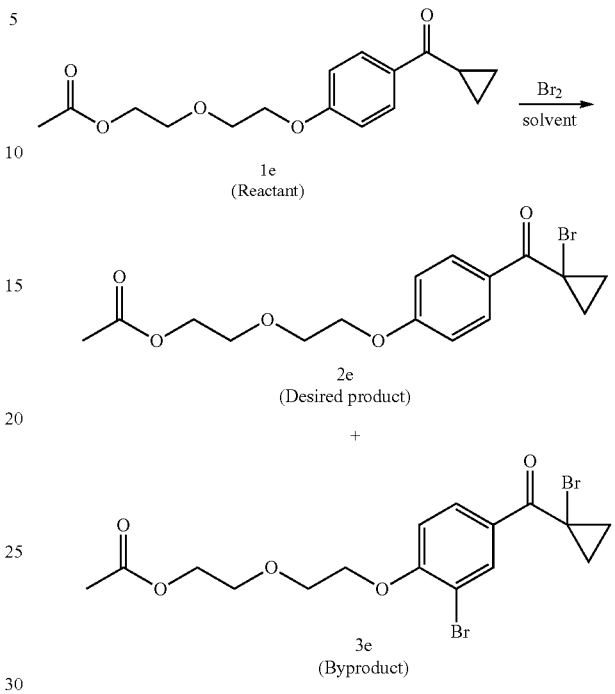

In the synthesis of the compound 2a in Example 1, a compound 2e was obtained in the same manner as in the synthesis of the compound 2a in Example 1 except for using a compound 1e instead of the compound 1a and changing the reaction condition to a reaction condition provided in the table below. In Reference Example 1 above, the compound 1e was synthesized in the same manner as in Reference Example 1, except for using cyclopropanecarbonyl chloride instead of isobutyryl chloride. Both of the compounds 1e and 2e were liquids at 5° C. to 30° C.

Purity of the obtained compound 2e was calculated based on a peak ratio of $^1$H-NMR (CDCl$_3$) in the same manner as in Example 1. Results thereof are provided in the table below.

Example 41

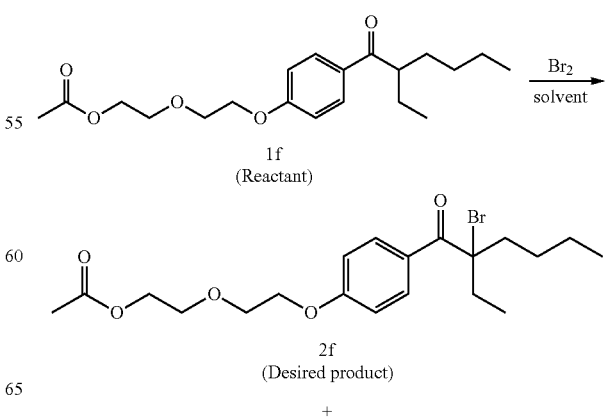

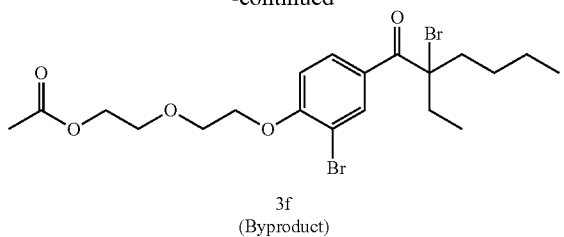

3f
(Byproduct)

In the synthesis of the compound 2a in Example 1, a compound 2f was obtained in the same manner as in Example 1, except for using a compound 1f instead of the compound 1a and changing the reaction condition to a reaction condition provided in the table below. In Reference Example 1 above, the compound 1f was synthesized in the same manner as in Reference Example 1, except for using 2-ethythexanoyl chloride instead of isobutyryl chloride. Both of the compounds 1f and 2f were liquids 5° C. to 30° C.

Purity of the obtained compound 2f was calculated based on the peak ratio of $^1$H-NMR (CDCl$_3$) in the same manner as in Example 1. The results are provided in the table below.

Example 42

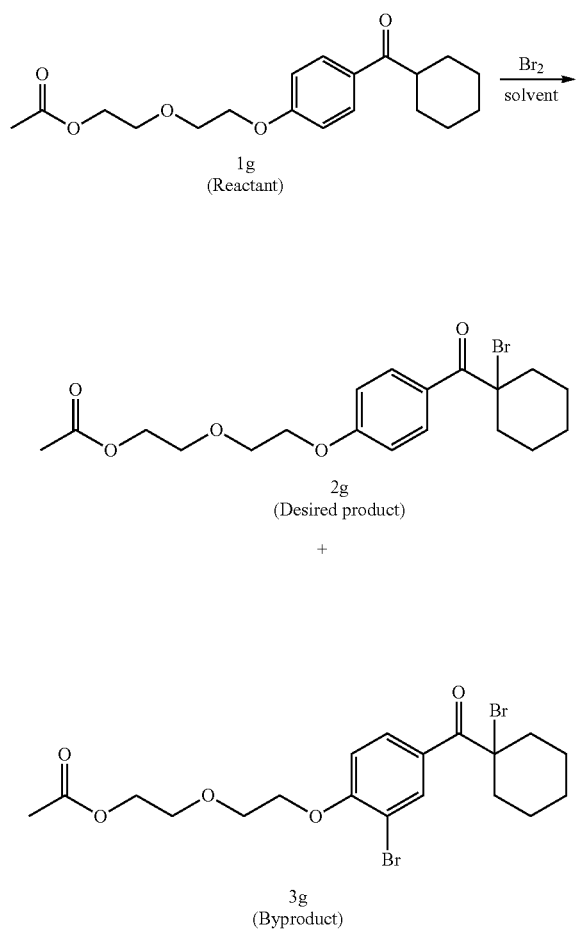

In the synthesis of the compound 2a in Example 1, a compound 2g was obtained in the same manner as in the synthesis of the compound 2a in Example 1, except for using a compound 1g instead of the compound 1a and changing the reaction condition to the reaction condition provided in the table below. In Reference Example 1 above, the compound 1g was synthesized in the same manner as in Reference Example 1, except for using cyclohexanecarbonyl chloride instead of isobutyryl chloride. Both of the compounds 1g and 2g were liquids at 5° C. to 30° C.

Purity of the obtained compound 2g was calculated based on a peak ratio of $^1$H-NMR (CDCl$_3$) in the same manner as in Example 1. The results are provided in the table below.

Comparative Example 1

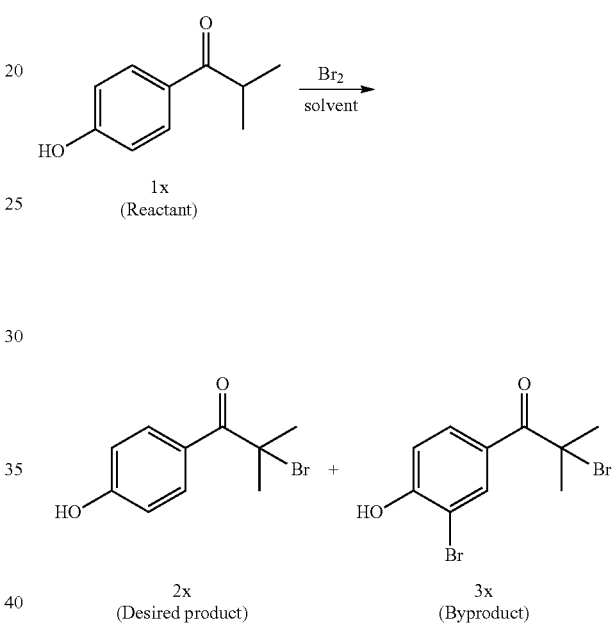

In the synthesis of the compound 2a in Example 1, a compound 2x was obtained in the same manner as in the synthesis of the compound 2a in Example 1, except for using a compound 1x instead of the compound 1a and changing the reaction condition to a reaction condition provided in the table below. The compound 1x was synthesized in the same manner as in the method disclosed in EP1073702B. Both of the compounds 1x and 2x were solids at 5° C. to 30° C. A melting point of the compound 2x was 56° C.

Purity of the obtained compound 2x was calculated based on a peak ratio of $^1$H-NMR (CDCl$_3$) in the same manner as in Example 1. Results thereof are provided in the table below.

Comparative Examples 2 to 15

In the synthesis of the compound 2a in Example 1, the compound 2a was obtained in the same manner as in the synthesis of the compound 2a in Example 1, except for changing the reaction condition to a reaction condition provided in the table below. Purity of the obtained compound 2a was measured in the same manner as in Example 1. Results thereof are provided in the table below.

TABLE 1

| | Examples | | | | | | |
|---|---|---|---|---|---|---|---|
| | | Reactant (Formula (1)) | | Bromine | | Reaction temperature [° C.] (Reaction liquid temperature in three-neck flask) | Dropwise addition time [min] |
| Example No. | Type | Vessel | Mixed solvent (Use amount [mL]) | Vessel | Mixed solvent (Use amount [mL]) | | |
| 1 | 1a | Three-neck flask | Ethyl acetate (12.5) | Dropwise addition funnel | Ethyl acetate (12.5) | 45 | 30 |
| 2 | 1a | Three-neck flask | Ethyl acetate (25) | Dropwise addition funnel | — | 45 | 30 |
| 3 | 1a | Three-neck flask | Ethyl acetate (12.5) | Dropwise addition funnel | 1,4-dioxane (12.5) | 45 | 30 |
| 4 | 1a | Three-neck flask | 1,4-dioxane (12.5) | Dropwise addition funnel | Ethyl acetate (12.5) | 45 | 30 |
| 5 | 1a | Dropwise addition funnel | Ethyl acetate (12.5) | Three-neck flask | Ethyl acetate (12.5) | 45 | 30 |
| 6 | 1a | Three-neck flask | Ethyl acetate (12.5) | Dropwise addition funnel | 1,4-dioxane (12.5) | 45 | 30 |
| 7 | 1a | Three-neck flask | Ethyl acetate (5) | Dropwise addition funnel | Ethyl acetate (20) | 45 | 30 |
| 8 | 1a | Three-neck flask | Ethyl acetate (10) | Dropwise addition funnel | Ethyl acetate (15) | 45 | 30 |
| 9 | 1a | Three-neck flask | Ethyl acetate (12.5) | Dropwise addition funnel | Ethyl acetate (12.5) | 20 | 30 |
| 10 | 1a | Three-neck flask | Ethyl acetate (12.5) | Dropwise addition funnel | Ethyl acetate (12.5) | 50 | 30 |
| 11 | 1a | Three-neck flask | Ethyl acetate (12.5) | Dropwise addition funnel | Ethyl acetate (12.5) | 55 | 30 |
| 12 | 1a | Three-neck flask | Ethyl acetate (12.5) | Dropwise addition funnel | Ethyl acetate (12.5) | 58 | 30 |
| 13 | 1a | Three-neck flask | Ethyl acetate (12.5) | Dropwise addition funnel | Ethyl acetate (12.5) | 30 | 30 |
| 14 | 1a | Three-neck flask | Ethyl acetate (12.5) | Dropwise addition funnel | Ethyl acetate (12.5) | 45 | 5 |
| 15 | 1a | Three-neck flask | Ethyl acetate (12.5) | Dropwise addition funnel | Ethyl acetate (12.5) | 45 | 20 |
| 16 | 1a | Three-neck flask | Ethyl acetate (12.5) | Dropwise addition funnel | Ethyl acetate (12.5) | 45 | 60 |
| 17 | 1a | Three-neck flask | Ethyl acetate (12.5) | Dropwise addition funnel | Ethyl acetate (12.5) | 45 | 120 |
| 18 | 1a | Three-neck flask | Ethyl acetate (12.5) | Dropwise addition funnel | Ethyl acetate (12.5) | 45 | 180 |
| 19 | 1a | Three-neck flask | Ethyl acetate (12.5) | Dropwise addition funnel | Ethyl acetate (20) | 45 | 30 |
| 20 | 1a | Three-neck flask | Ethyl acetate (12.5) | Dropwise addition funnel | Ethyl acetate (15) | 45 | 30 |
| 21 | 1a | Three-neck flask | Ethyl acetate (12.5) | Dropwise addition funnel | Ethyl acetate (12.5) | 45 | 30 |
| 22 | 1a | Three-neck flask | Ethyl acetate (12.5) | Dropwise addition funnel | Ethyl acetate (12.5) | 45 | 30 |

TABLE 1-continued

| | | | | | | | |
|---|---|---|---|---|---|---|---|
| 23 | 1a | Three-neck flask | Ethyl acetate (12.5) | Dropwise addition funnel | Ethyl acetate/dibutyl ether = 8/2 (volume ratio) (12.5) | 45 | 30 |
| 24 | 1a | Three-neck flask | Ethyl acetate (3.5) | Dropwise addition funnel | Ethyl acetate (3.5) | 45 | 30 |
| 25 | 1a | Three-neck flask | Ethyl acetate (5.0) | Dropwise addition funnel | Ethyl acetate (5.0) | 45 | 30 |
| 26 | 1a | Three-neck flask | Ethyl acetate (7.5) | Dropwise addition funnel | Ethyl acetate (7.5) | 45 | 30 |
| 27 | 1a | Three-neck flask | Ethyl acetate (50) | Dropwise addition funnel | Ethyl acetate (50) | 45 | 30 |
| 28 | 1a | Three-neck flask | Ethyl acetate (600) | Dropwise addition funnel | Ethyl acetate (600) | 45 | 30 |
| 29 | 1a | Three-neck flask | Methyl acetate (12.5) | Dropwise addition funnel | Methyl acetate (12.5) | 45 | 30 |
| 30 | 1a | Three-neck flask | Methyl acetate (12.5) | Dropwise addition funnel | Methyl acetate (12.5) | 20 | 30 |
| 31 | 1a | Three-neck flask | Butyl acetate (12.5) | Dropwise addition funnel | Butyl acetate (12.5) | 45 | 30 |
| 32 | 1a | Three-neck flask | Butyl acetate (12.5) | Dropwise addition funnel | Butyl acetate (12.5) | 20 | 30 |
| 33 | 1a | Three-neck flask | Propyl acetate (12.5) | Dropwise addition funnel | Propyl acetate (12.5) | 45 | 30 |
| 34 | 1a | Three-neck flask | Propyl acetate (12.5) | Dropwise addition funnel | Propyl acetate (12.5) | 20 | 30 |
| 35 | 1a | Three-neck flask | Isopropyl acetate (12.5) | Dropwise addition funnel | Isopropyl acetate (12.5) | 45 | 30 |
| 36 | 1a | Three-neck flask | Isopropyl acetate (12.5) | Dropwise addition funnel | Isopropyl acetate (12.5) | 20 | 30 |
| 37 | 1a | Three-neck flask | Methyl propionate (12.5) | Dropwise addition funnel | Methyl propionate (12.5) | 45 | 30 |
| 38 | 1a | Three-neck flask | Methyl propionate (12.5) | Dropwise addition funnel | Methyl propionate (12.5) | 20 | 30 |
| 39 | 1d | Three-neck flask | Ethyl acetate (12.5) | Dropwise addition funnel | Ethyl acetate (12.5) | 45 | 30 |
| 40 | 1e | Three-neck flask | Ethyl acetate (12.5) | Dropwise addition funnel | Ethyl acetate (12.5) | 45 | 30 |
| 41 | 1f | Three-neck flask | Ethyl acetate (12.5) | Dropwise addition funnel | Ethyl acetate (12.5) | 45 | 30 |
| 42 | 1g | Three-neck flask | Ethyl acetate (12.5) | Dropwise addition funnel | Ethyl acetate (12.5) | 45 | 30 |
| 43 | 1a | Three-neck flask | Ethyl acetate (12.5) | Dropwise addition funnel | Ethyl acetate (12.5) | 10 | 30 |
| 44 | 1a | Three-neck flask | Ethyl acetale (12.5) | Dropwise addition funnel | Ethyl acetate (12.5) | 5 | 30 |
| 45 | 1a | Three-neck flask | Ethyl acetate (12.5) | Dropwise addition funnel | Ethyl acetate (12.5) | −5 | 30 |

TABLE 1-continued

| | Examples | | | | | |
|---|---|---|---|---|---|---|
| | Use amount of solvent with respect to 1 g of reactant (Formula (1)) [mL] | Bromine/reactant (Formula (1)) [molar ratio] | Desired product (Formula (2)) | Composition of reaction product (mol %) | | |
| Example No. | | | | Desired product (Formula (2)) | Reactant (Formula (1)) | Byproduct (Benzene ring bromination) |
| 1 | 2.5 | 1.05 | 2a | 100 | 0 | 0 |
| 2 | 2.5 | 1.05 | 2a | 100 | 0 | 0 |
| 3 | 2.5 | 1.05 | 2a | 100 | 0 | 0 |
| 4 | 2.5 | 1.05 | 2a | 100 | 0 | 0 |
| 5 | 2.5 | 1.05 | 2a | 98.5 | 0 | 1.5 |
| 6 | 2.5 | 1.05 | 2a | 100 | 0 | 0 |
| 7 | 2.5 | 1.05 | 2a | 98.6 | 0 | 1.4 |
| 8 | 2.5 | 1.05 | 2a | 99.0 | 0 | 1.0 |
| 9 | 2.5 | 1.05 | 2a | 99.2 | 0 | 0.8 |
| 10 | 2.5 | 1.05 | 2a | 100 | 0 | 0 |
| 11 | 2.5 | 1.05 | 2a | 100 | 0 | 0 |
| 12 | 2.5 | 1.05 | 2a | 99.9 | 0.1 | 0 |
| 13 | 2.5 | 1.05 | 2a | 99.9 | 0 | 0.1 |
| 14 | 2.5 | 1.05 | 2a | 97.6 | 0 | 2.4 |
| 15 | 2.5 | 1.05 | 2a | 100 | 0 | 0 |
| 16 | 2.5 | 1.05 | 2a | 100 | 0 | 0 |
| 17 | 2.5 | 1.05 | 2a | 100 | 0 | 0 |
| 18 | 2.5 | 1.05 | 2a | 100 | 0 | 0 |
| 19 | 2.5 | 1.1 | 2a | 100 | 0 | 0 |
| 20 | 2.5 | 1.3 | 2a | 97.2 | 0 | 2.8 |
| 21 | 2.5 | 1.00 | 2a | 100 | 0 | 0 |
| 22 | 2.5 | 0.95 | 2a | 95.5 | 4.5 | 0 |
| 23 | 2.5 | 1.05 | 2a | 100 | 0 | 0 |
| 24 | 0.7 | 1.05 | 2a | 94.5 | 0 | 5.5 |
| 25 | 1.0 | 1.05 | 2a | 96.5 | 0 | 3.5 |
| 26 | 1.5 | 1.05 | 2a | 99.5 | 0 | 0.5 |
| 27 | 10 | 1.05 | 2a | 100 | 0 | 0 |
| 28 | 120 | 1.05 | 2a | 100 | 0 | 0 |
| 29 | 2.5 | 1.05 | 2a | 100 | 0 | 0 |
| 30 | 2.5 | 1.05 | 2a | 98.1 | 0 | 1.9 |
| 31 | 2.5 | 1.05 | 2a | 100 | 0 | 0 |
| 32 | 2.5 | 1.05 | 2a | 97.9 | 0 | 2.1 |
| 33 | 2.5 | 1.05 | 2a | 100 | 0 | 0 |
| 34 | 2.5 | 1.05 | 2a | 98.2 | 0 | 1.8 |
| 35 | 2.5 | 1.05 | 2a | 100 | 0 | 0 |
| 36 | 2.5 | 1.05 | 2a | 98.3 | 0 | 1.7 |
| 37 | 2.5 | 1.05 | 2a | 100 | 0 | 0 |
| 38 | 2.5 | 1.05 | 2a | 98.2 | 0 | 1.8 |
| 39 | 2.5 | 1.05 | 2d | 99.4 | 0 | 0.6 |
| 40 | 2.5 | 1.05 | 2e | 99.5 | 0 | 0.5 |
| 41 | 2.5 | 1.05 | 2f | 98.0 | 0 | 2.0 |
| 42 | 2.5 | 1.05 | 2g | 97.9 | 0 | 2.1 |
| 43 | 2.5 | 1.05 | 2a | 98.3 | 0 | 1.7 |
| 44 | 2.5 | 1.05 | 2a | 96.7 | 0 | 3.3 |
| 45 | 2.5 | 1.05 | 2a | 95.4 | 0 | 4.6 |

TABLE 2

| | Comparative Examples | | | | | | |
|---|---|---|---|---|---|---|---|
| | Reactant | | | Bromine | | Reaction temperature [° C.] (Reaction liquid temperature in three-neck flask) | Dropwise addition time [min] |
| Comparative Example No. | Type | Vessel | Mixed solvent (Use amount [mL]) | Vessel | Mixed solvent (Use amount [mL]) | | |
| 1 | 1x | Three-neck flask | Butyl acetate (12.5) | Dropwise addition funnel | Butyl acetate (12.5) | 20 | 30 |
| 2 | 1a | Three-neck flask | Glacial acetic acid (12.5) | Dropwise addition funnel | Glacial acetic acid (12.5) | 45 | 30 |

TABLE 2-continued

| | | | | | | | |
|---|---|---|---|---|---|---|---|
| 3 | 1a | Three-neck flask | Glacial acetic acid (12.5) | Dropwise addition funnel | Glacial acetic acid (12.5) | 20 | 30 |
| 4 | 1a | Three-neck flask | Glacial acetic acid (12.5) | Dropwise addition funnel | Glacial acetic acid (12.5) | 20 | 30 |
| 5 | 1a | Three-neck flask | Dichloromethane (12.5) | Dropwise addition funnel | Dichloromethane (12.5) | 45 | 30 |
| 6 | 1a | Three-neck flask | Dichloromethane (12.5) | Dropwise addition funnel | Dichloromethane (12.5) | 20 | 30 |
| 7 | 1a | Three-neck flask | Dichloromethane (12.5) | Dropwise addition funnel | Dichloromethane (12.5) | 20 | 30 |
| 8 | 1a | Three-neck flask | Methanol (12.5) | Dropwise addition funnel | Methanol (12.5) | 45 | 30 |
| 9 | 1a | Three-neck flask | Methanol (12.5) | Dropwise addition funnel | Methanol (12.5) | 20 | 30 |
| 10 | 1a | Three-neck flask | Carbon tetrachloride (12.5) | Dropwise addition funnel | Carbon tetrachloride (12.5) | 45 | 30 |
| 11 | 1a | Three-neck flask | Carbon tetrachloride (12.5) | Dropwise addition funnel | Carbon tetrachloride (12.5) | 20 | 30 |
| 12 | 1a | Three-neck flask | Acetic acid (12.5) | Dropwise addition funnel | Acetic acid (12.5) | 45 | 30 |
| 13 | 1a | Three-neck flask | Acetic acid (12.5) | Dropwise addition funnel | Acetic acid (12.5) | 20 | 30 |
| 14 | 1a | Three-neck flask | Chlorobenzene (12.5) | Dropwise addition funnel | Chlorobenzene (12.5) | 45 | 30 |
| 15 | 1a | Three-neck flask | Chlorobenzene (12.5) | Dropwise addition funnel | Chlorobenzene (12.5) | 20 | 30 |

Comparative Exmaples

| | Use amount of solvent with respect to 1 g of reactant (Formula (1)) [mL] | Bromine/reactant (Formula (1)) [molar ratio] | Desired product (Formula (2)) | Composition of reaction product (mol %) | | |
|---|---|---|---|---|---|---|
| Comparative Example No. | | | | Desired product (Formula (2)) | Reactant (Formula (1)) | Byproduct (Benzene ring bromination) |
| 1 | 2.5 | 1.05 | 2x | 88.5 | 0 | 11.5 |
| 2 | 2.5 | 1.05 | 2a | 89.5 | 0 | 10.5 |
| 3 | 2.5 | 1.05 | 2a | 89.3 | 0.5 | 10.2 |
| 4 | 0.8 | 1.05 | 2a | 84.2 | 0.6 | 15.2 |
| 5 | 2.5 | 1.05 | 2a | 86.8 | 0 | 13.2 |
| 6 | 2.5 | 1.05 | 2a | 88.2 | 1.5 | 10.3 |
| 7 | 0.8 | 1.05 | 2a | 83.4 | 1.2 | 15.4 |
| 8 | 2.5 | 1.05 | 2a | 70.7 | 13.2 | 16.1 |
| 9 | 2.5 | 1.05 | 2a | 73 | 12.2 | 14.8 |
| 10 | 2.5 | 1.05 | 2a | 83.7 | 1.5 | 14.8 |
| 11 | 2.5 | 1.05 | 2a | 84.6 | 2.3 | 13.1 |
| 12 | 2.5 | 1.05 | 2a | 87.6 | 0.7 | 11.7 |
| 13 | 2.5 | 1.05 | 2a | 87.9 | 0.9 | 11.2 |
| 14 | 2.5 | 1.05 | 2a | 61.7 | 22.1 | 16.2 |
| 15 | 2.5 | 1.05 | 2a | 60.6 | 28.9 | 10.5 |

From the results in Comparative Example 1 above, in a case where a compound in which n in Formula (1) was smaller than that of the invention was used as a reactant, even if the solvent regulated in the invention was used, it was resulted that selectivity of the bromination was low and purity of the obtained desired α-bromoacetophenone compound was low.

From the results of Comparative Examples 2 to 15 above, if the used solvent didn't include at least one organic acid ester compound, it was also resulted that selectivity of the bromination was low and purity of the obtained desired α-bromoacetophenone compound was low.

In contrast, in Examples 1 to 45 in which all of the requirements regulated in the invention are satisfied, it was understood that selectivity of the bromination was greatly increased and the α-bromoacetophenone compound in which recrystallization was difficult was able to be obtained with high reaction purity.

What is claimed is:
1. A method for manufacturing an α-bromoacetophenone compound of Formula (2) below, comprising:

brominating a phenyl compound of Formula (1) below by reacting the phenyl compound with bromine in a solvent including at least one organic acid ester compound to produce the α-bromoacetophenone compound of Formula (2), wherein the α-bromoacetophenone compound is a liquid at 5° C. to 30° C., and a total content of the organic acid ester compound is 50 to 100 mass % of a total amount of the solvent used in the bromination,

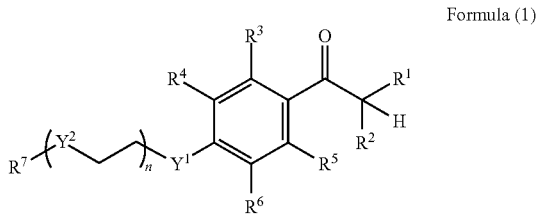

Formula (1)

in Formula (1), $R^1$ and $R^2$ each independently represent an alkyl group, $R^3$ to $R^6$ each independently represent a hydrogen atom or a substituent, at least one of $R^3$, $R^4$, $R^5$, or $R^6$ is a hydrogen atom, $Y^1$ and $Y^2$ each independently represent an oxygen atom or a sulfur atom, n represents 2 to 3, and $R^7$ represents a hydrogen atom, an alkyl group, an acyl group, or a trialkylsilyl group, and

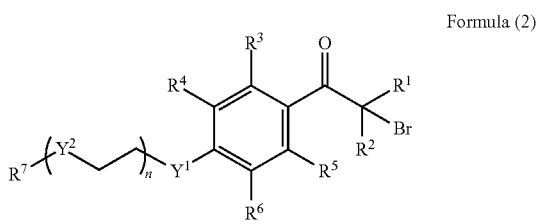

Formula (2)

in Formula (2), $R^1$ to $R^7$, $Y^1$, $Y^2$, and n each have the same meaning as $R^1$ to $R^7$, $Y^1$, $Y^2$, and n in Formula (1) above.

2. The method for manufacturing an α-bromoacetophenone compound according to claim 1,
wherein a reaction temperature of the bromination is 20° C. or greater.

3. The method for manufacturing an α-bromoacetophenone compound according to claim 1,
wherein the solvent including at least one organic acid ester compound is selected from the group consisting of methyl acetate, ethyl acetate, butyl acetate, propyl acetate, isopropyl acetate, and a combination thereof.

4. The method for manufacturing an α-bromoacetophenone compound according to claim 1,
wherein a reaction temperature of the bromination is 40° C. or greater.

5. The method for manufacturing an α-bromoacetophenone compound according to claim 3,
wherein a reaction temperature of the bromination is 40° C. or greater.

6. The method for manufacturing an α-bromoacetophenone compound according to claim 1,
wherein an amount of the solvent including at least one organic acid ester compound is 0.5 to 60 mL per 1 g of the phenyl compound in a reaction liquid which is all of the solvent, bromine, and the phenyl compound.

7. The method for manufacturing an α-bromoacetophenone compound according to claim 1,
wherein the solvent including at least one organic acid ester compound is a liquid and the bromination is performed by adding the bromine or a mixture comprising bromine and the liquid solvent including at least one organic acid ester compound dropwise into a mixture comprising the phenyl compound and the liquid solvent including at least one organic acid ester compound, or
the bromination is performed by adding a mixture comprising the bromine and the liquid solvent including at least one organic acid ester compound dropwise into the phenyl compound or a mixture comprising the phenyl compound and the liquid solvent including at least one organic acid ester compound.

8. The method for manufacturing an α-bromoacetophenone compound according to claim 7,
wherein the bromination is performed by adding the mixture comprising the bromine and the liquid solvent including at least one organic acid ester compound dropwise into the mixture comprising the phenyl compound and the liquid solvent including at least one organic acid ester compound.

9. The method for manufacturing an α-bromoacetophenone compound according to claim 8,
wherein a ratio of an amount A of the solvent including at least one organic acid ester compound in the mixture comprising the bromine and the liquid solvent including at least one organic acid ester compound and an amount B of the liquid solvent including at least one organic acid ester compound in the mixture comprising the phenyl compound and the liquid solvent including at least one organic acid ester compound satisfies B:A=90:10 to 30:70 in a volume ratio.

10. The method for manufacturing an α-bromoacetophenone compound according to claim 1,
wherein a total content of the organic acid ester compound is 70 to 100 mass % of a total amount of the solvent used in the bromination.

11. The method for manufacturing an α-bromoacetophenone compound according to claim 3,
wherein a total content of the organic acid ester compound is 70 to 100 mass % of a total amount of the solvent used in the bromination.

12. The method for manufacturing an α-bromoacetophenone compound according to claim 4,
wherein a total content of the organic acid ester compound is 70 to 100 mass % of a total amount of the solvent used in the bromination.

13. The method for manufacturing an α-bromoacetophenone compound according to claim 5,
wherein a total content of the organic acid ester compound is 70 to 100 mass % of a total amount of the solvent used in the bromination.

14. The method for manufacturing an α-bromoacetophenone compound according to claim 1,
wherein the solvent including at least one organic acid ester compound is selected from the group consisting of methyl acetate, ethyl acetate, propyl acetate, isopropyl acetate, butyl acetate, methyl propionate, ethyl propionate, propyl propionate, isopropyl propionate, butyl propionate, and a combination thereof.

* * * * *